United States Patent [19]

Mikhail et al.

[11] Patent Number: 5,108,405

[45] Date of Patent: Apr. 28, 1992

[54] SYSTEM FOR PERFORMING HIP PROSETHESIS REVISION SURGERY

[76] Inventors: W. E. Michael Mikhail, 4203 Shamley Green, Toledo, Ohio 43623; James J. Elting, 35 Academy St., Oneonta, N.Y. 13620

[21] Appl. No.: 710,503

[22] Filed: Jun. 4, 1991

Related U.S. Application Data

[62] Division of Ser. No. 565,149, Aug. 10, 1990, Pat. No. 5,047,035.

[51] Int. Cl.⁵ .............................. A61B 17/56
[52] U.S. Cl. ............................ 606/96; 606/80
[58] Field of Search .............. 606/79, 80, 96, 99

[56] References Cited

U.S. PATENT DOCUMENTS

| | | | |
|---|---|---|---|
| 4,341,206 | 7/1982 | Perrett et al. | 606/80 |
| 4,678,471 | 7/1987 | Noble et al. | 606/80 X |
| 4,686,972 | 8/1987 | Kurland | 606/96 |
| 4,706,659 | 11/1987 | Mathews et al. | 606/80 |
| 4,751,922 | 6/1988 | DiPietropolo | 606/80 |
| 4,846,161 | 7/1989 | Roger | 606/82 |
| 4,860,735 | 8/1989 | Davey et al. | 606/80 |
| 4,873,969 | 10/1989 | Huebsch | 606/80 |
| 4,881,536 | 11/1989 | Noble et al. | 606/94 |
| 4,919,153 | 4/1990 | Chin | 606/93 |
| 4,919,673 | 4/1990 | Willert et al. | 623/23 |
| 4,919,679 | 4/1990 | Averill et al. | 623/23 |
| 4,986,826 | 1/1991 | Roger | 606/82 |
| 4,994,085 | 2/1991 | Sawai et al. | 623/23 |

OTHER PUBLICATIONS

Article entitled "Economy is the mother of a cement removal technique", *Orthopedics Today*, pp. 18 & 19, Sep. 1989.

*Primary Examiner*—Robert A. Hafer
*Assistant Examiner*—Kevin G. Rooney
*Attorney, Agent, or Firm*—Emch, Schaffer, Schaub & Porcello Co., L.P.A.

[57] ABSTRACT

A system for performing hip prosthesis revision surgery includes a trial femoral component having a passageway which, upon insertion in the cavity left after removal of the original prosthesis, provides guide means for drilling a channel to receive a guide wire which, upon removal of the trial femoral component, serves as guide means for progressively larger reamers.

5 Claims, 5 Drawing Sheets

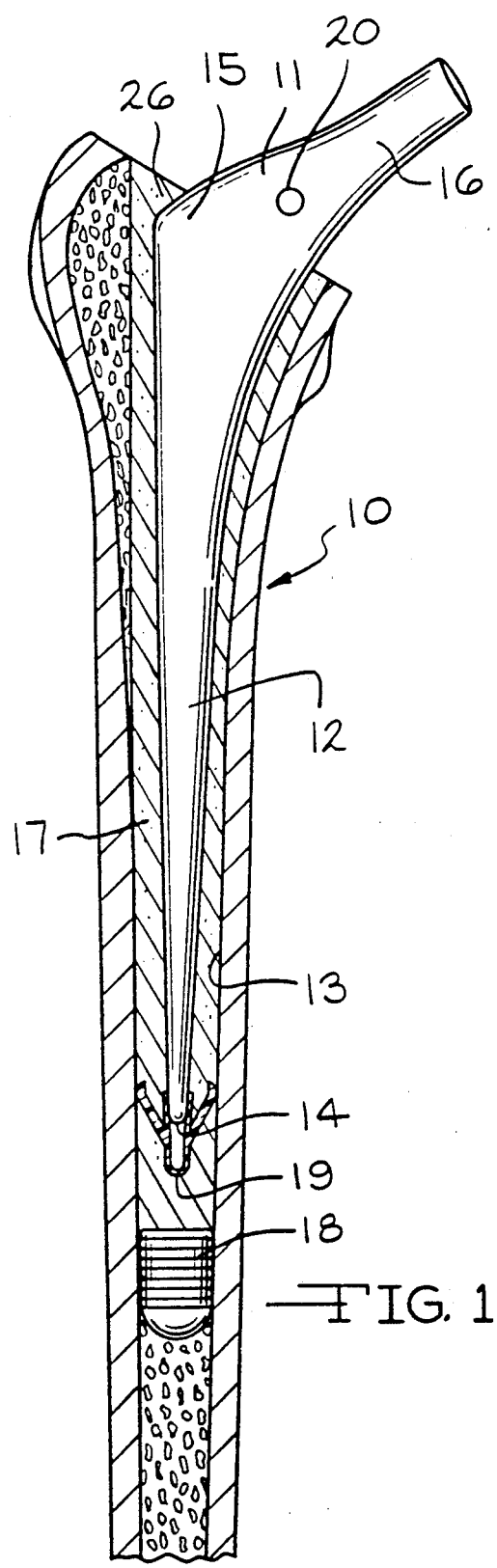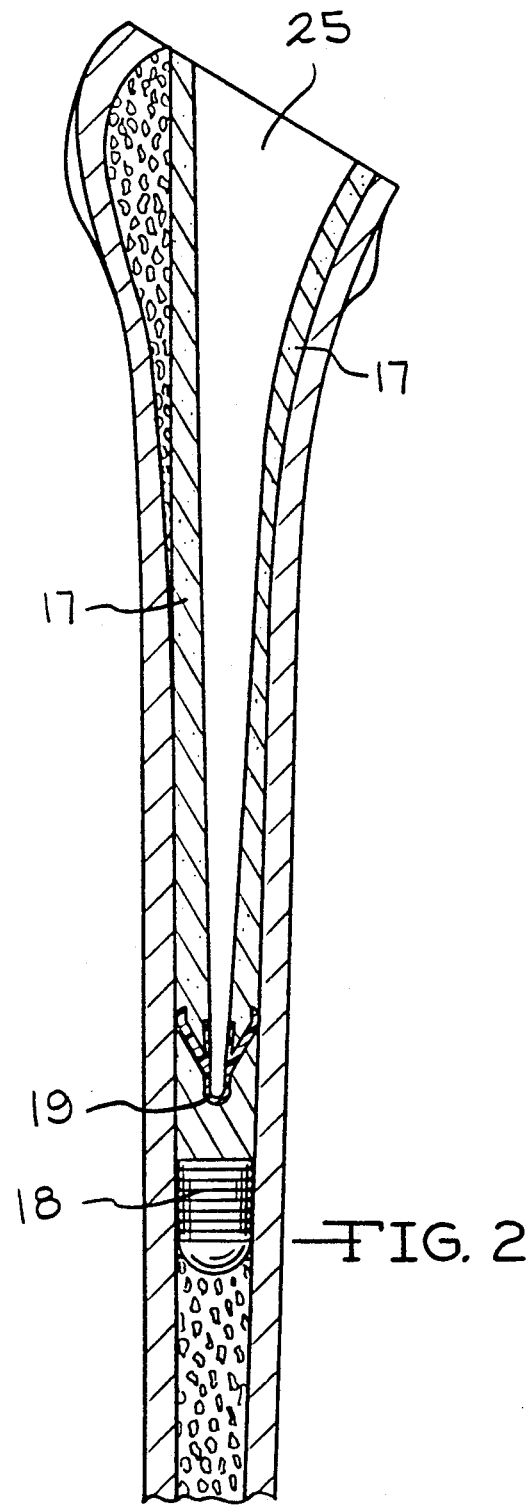

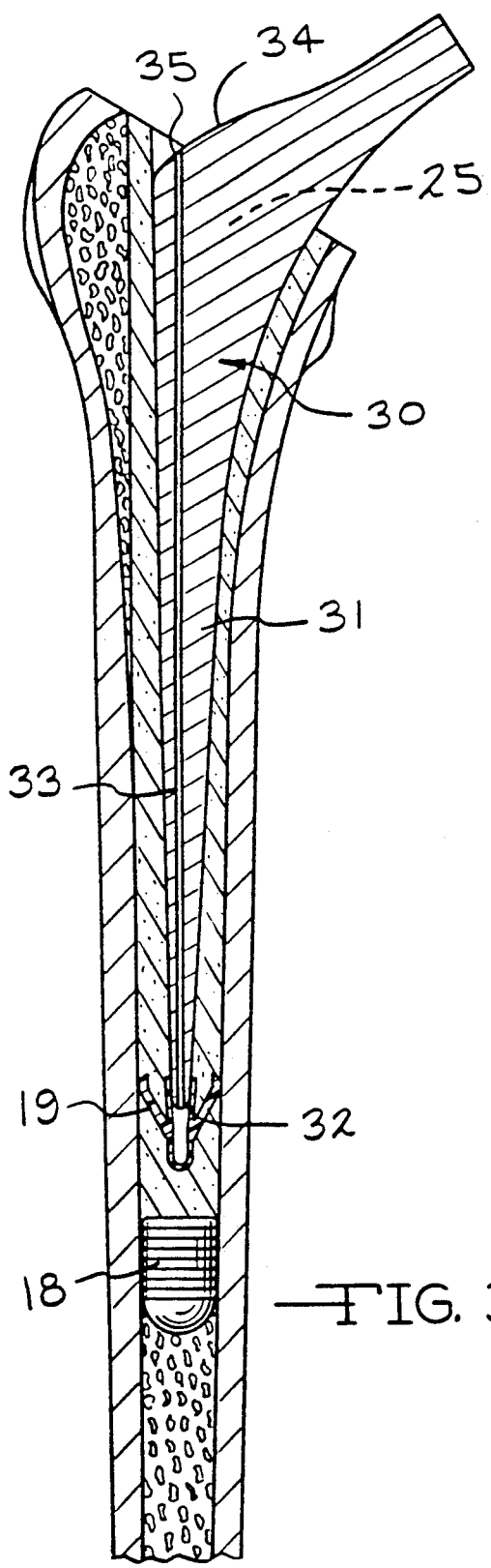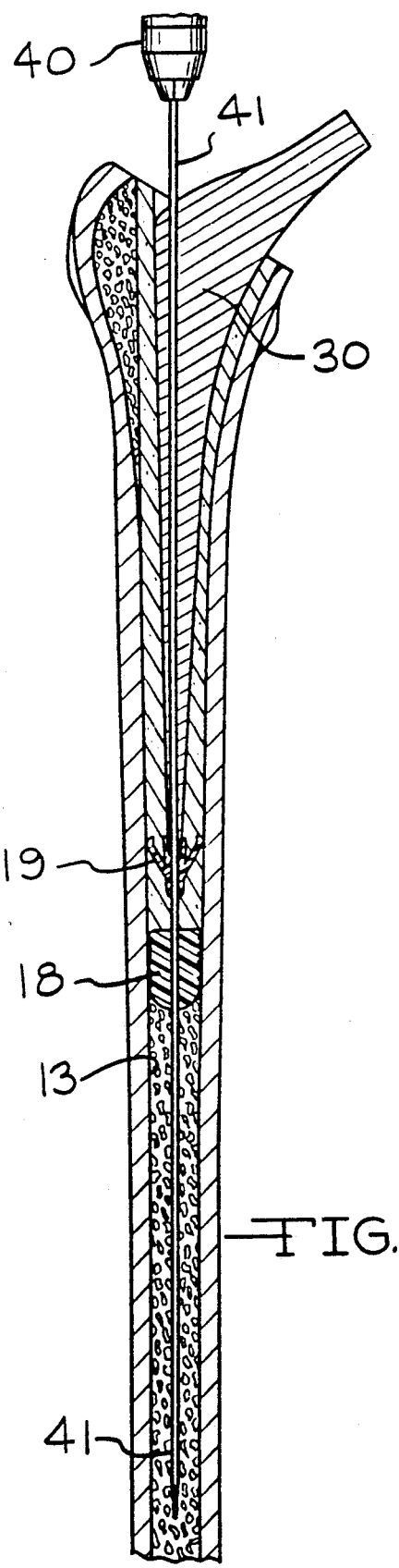
FIG. 3
FIG. 4

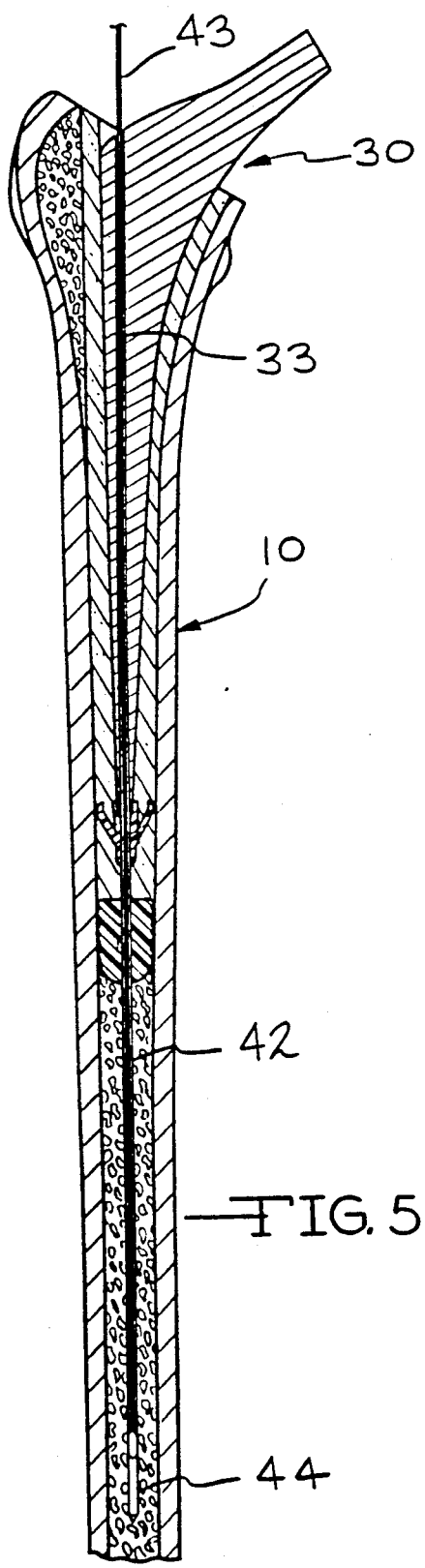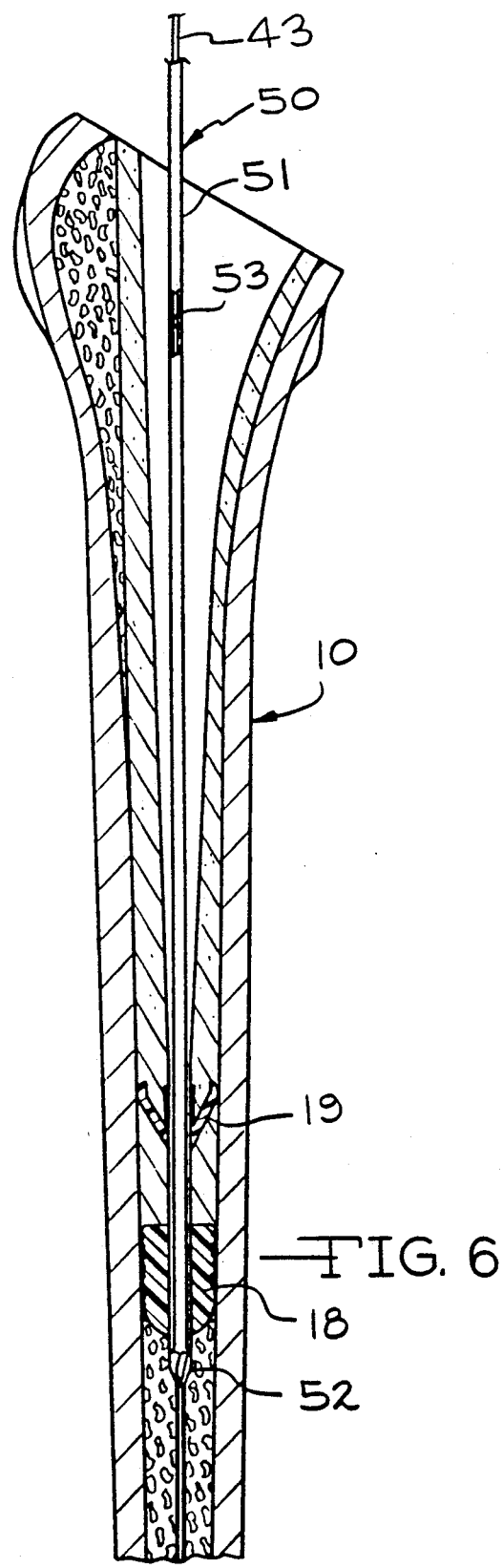

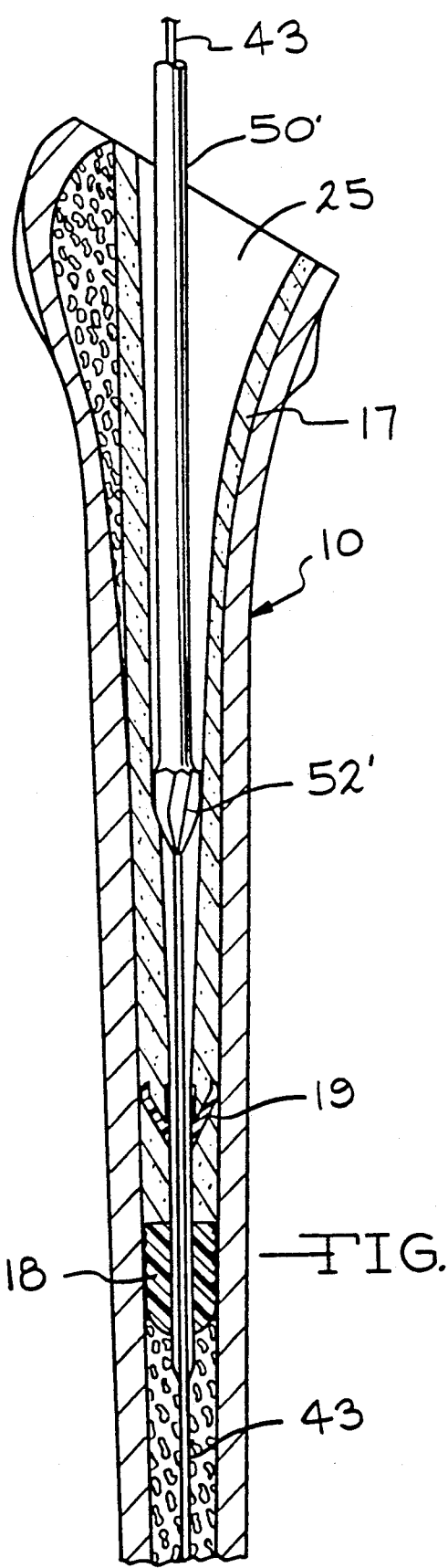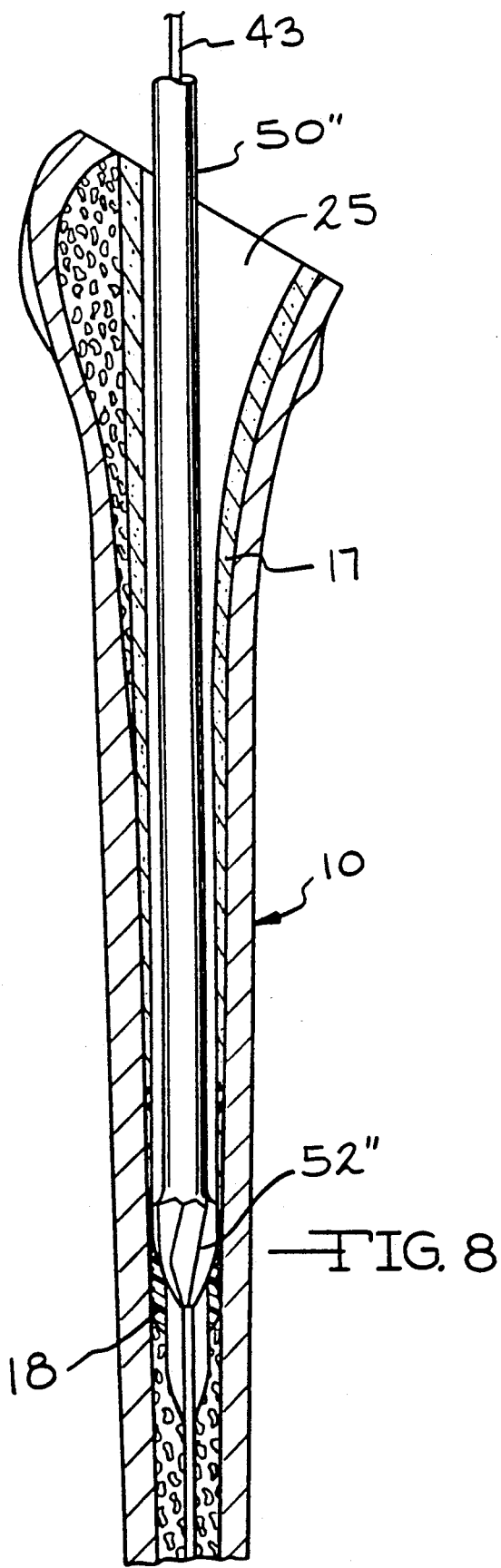

SYSTEM FOR PERFORMING HIP PROSETHESIS REVISION SURGERY

This is a divisional of copending application Ser. No. 07/565,149 filed on Aug. 10, 1990, now U.S. Pat. No. 5,047,035.

BACKGROUND OF THE INVENTION

The present invention is directed to a system for performing revision surgery to replace a hip prosthesis having a stem portion previously implanted in a cement mantle in the intramedullary canal of a femur and to a system for performing such surgery.

As is well known, it is frequently necessary to replace a hip joint prosthesis. This is usually done several years after the original implantation in order to replace disfunctional joints or to obtain the benefits of one of newer design which resulted from advancements in medical technology.

In the course of hip revision surgery, it is necessary to remove the femoral component including its stem form the intramedullary canal of the femur. The cement material utilized to fix the stem within the intramedullary canal must be removed prior to implantation of the new prosthesis therein. Removal of the cement is accomplished by drilling or reaming. During such drilling or reaming procedure, it is important that the drill or reamer or properly aligned and guided to avoid accidental perforation of the cortex of the femur.

A number of prior art devices have been utilized for aligning drills or reamers in the performance of revision hip surgery. U.S. Pat. No. 4,860,735 relates to a drill alignment guide for osteoplastic surgery in which an alignment rod is supported on a clamp element affixed to the femur. The drill is mounted for movement with an alignment rod which is parallel to and disposed a predetermined distance from a shaft of the drill. As the drill is moved forward, the forward end of the alignment rod moves through an aperture of the clamp element thereby insuring that drilling occurs along a predetermined drilled path extending along the bone axis.

U.S. Pat. No. 4,686,972 relates to a surgical deflector and drilling guide for guiding a drill bit, awl or reamer into a bone. The boring-tool guide assembly comprises a sleeve having a T-shaped nib which can be detachably inserted into a corresponding bracket permanently mounted against a tool having teeth designed to anchor the tool in a boney tissue. The surgeon can insert the tip of a drill bit, awl or reamer into the sleeve of the guide assembly when the teeth are anchored onto a boney tissue to obtain means for guiding the boring tool.

A method of economically removing cement from the femoral canal during revision surgery appeared in the publication "Orthopedics Today", September 1989, pages 18 and 19. Under the procedure described therein, a side cut and end cut reamer positioned in a guide sleeve is utilized to remove the cement.

A catalog entitled "Omiflex TM Femoral System Surgical Protocol Press-Fit" copyright 1988 by Osteonics Corp., describes a cement removal system utilizing a tapered axial reamer.

U.S. Pat. No. 4,919,673 is directed to a femoral head prosthesis having a fixing stem with a longitudinal bore utilizing a centering rod extending therethrough and engaged to a barrier at the lower end of the bone cavity.

The foregoing prior art references are incorporated herein by reference and copes are herewith enclosed.

SUMMARY OF THE INVENTION

The present invention provides for a new system of performing revision surgery utilizing improved means for insuring proper centering and guidance for of the reamer utilized for removing old bone cement. Such centering and guidance means insures proper positioning of the revision prosthesis with an adequate thickness of bone cement there around and assists in avoiding accidental perforation of the cortex of the femur. Under the present invention, the original femoral component is removed and then replaced by a cannulated trial femoral component of similar size and shape to the original prosthesis which has been removed. X-rays taken prior to removal of the original prosthesis can be used to confirm that the original prosthesis is still properly aligned in the femoral canal and did not subside within the original cement mantle into varus. Assuming that the original prosthesis as removed was properly aligned, the cannulated trial femoral component is then inserted into the cavity left by the removal of the original prosthesis. An elongated drill is then inserted through the cannulated stem and, using the passageway of the cannulated stem as a guide, is utilized to drill through the cement and cement restricter at the bottom of the cavity thus forming a pilot hole in the cement, restricter and bone marrow therebelow. The pilot hole is sufficiently large to permit insertion of a bullit guide wire having a slightly enlarged head at its free end. Following insertion of the bullit guide wire, cannulated reamers of progressively increasing size are placed over the bullit guide wire and utilized to progressively increase the size of the prepared canal to (1) remove all of the old bone cement, centralizer and restrictor and (2) reach a size suitable for receiving new bone cement and the stem of the new femoral hip joint prosthesis.

The invention will be more fully understood and other objects and advantages will becomes apparent form the following detailed description in conjunction with the attached drawings.

BRIEF DESCRIPTION OF THE DRAWINGS

FIG. 1 is an elevational view, partially in section, showing the femoral hip joint prosthesis implanted in the femoral canal of a patient.

FIG. 2 is a view similar to FIG. 1 showing the femur with the previously implanted femoral hip joint prosthesis removed.

FIG. 3 is a view similar to FIGS. 1 and 2 showing the cannulated trial femoral component of the present invention positioned within the cavity previously occupied by the original femoral hip joint prosthesis.

FIG. 4 is a view similar to FIG. 3 but showing the drilling of a pilot passageway utilizing the cannulated trial femoral component as a guide.

FIG. 5 is a view similar to FIG. 4 following removal of the elongated drill bit and insertion of the guide wire with its enlarged bullit head through the guide passageway of the cannulated trial femoral component and into the newly drilled pilot hole.

FIG. 6 is a view similar to FIG. 5 but slightly enlarged for clarity, showing the reaming of the canal following removal of the cannulated trial stem and showing the first of several progressively larger reamers being utilized with the bullit guide wire as a guide to control the path of the reamer.

FIGS. 7 and 8 are view similar to FIG. 6 showing the femur as the canal is progressively enlarged with still larger reamers utilizing the bullit guide wire as a guide.

DESCRIPTION OF THE PREFERRED EMBODIMENT

Figure 9:
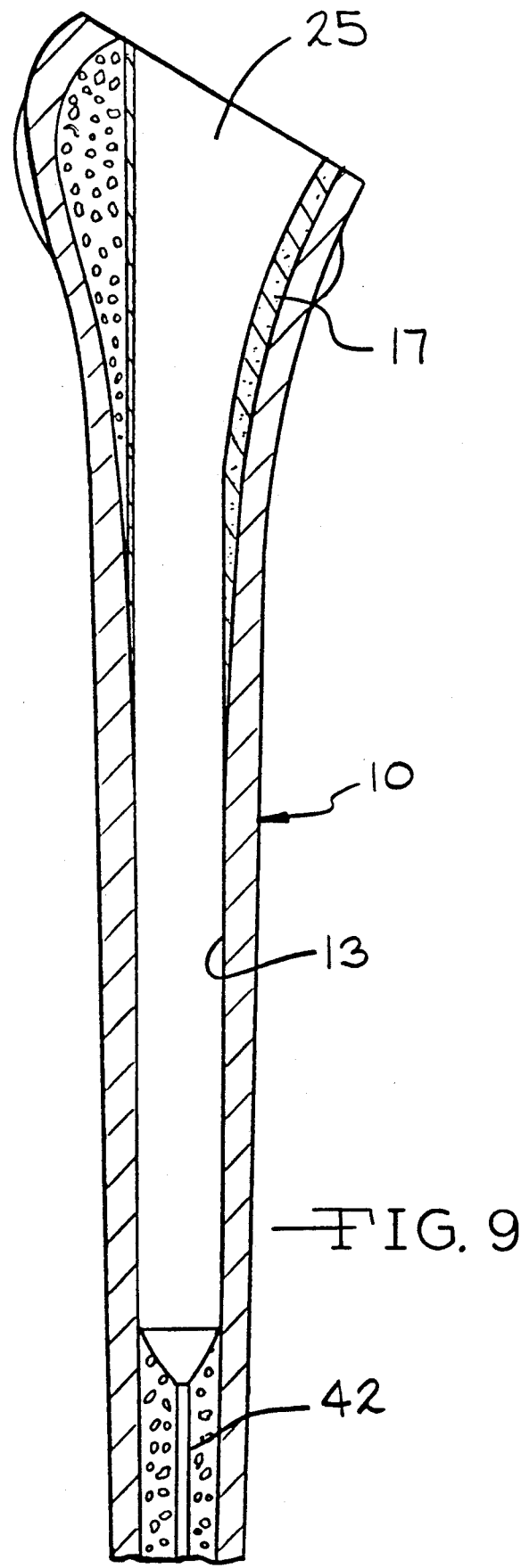
FIG. 9 is a sectional view of a femur prepared for revision surgery with the old cement removed and the guide wire removed.

Referring now to FIG. 1, there is shown a femur generally designated by the number 10 having implanted therein a hip joint prosthesis 11 having a stem 12 implanted within the intramedullary canal 13 of the femur. The stem extends from a lower distal end 14 to an upper portion which includes an enlarged shoulder 15 and a neck portion 16 disposed at an obtuse angle relative to the stem 12.

The prosthesis 11 is typically secured in the femoral intramedullary canal 13 by a cement mantle 17 of polymethylmethacrylate (PMMA) or other suitable bone cement. A restrictor 18 is placed in the intramedullary canal 13 prior to introduction of the bone cement 17 therein. The distal end 14 of the stem may be engaged in a centralizer 19 which assists in centering the distal end 14 during the step of implantation of the prosthesis 11 in the cement 17. The prosthesis 11 may be provided with an aperture 20 or other suitable grasping means to assist in its removal. As shown in FIG. 2, the removal of the prosthesis 11 leaves a cavity 25 conforming to the shape of the removed stem 12. Obviously, prior to removal of the prosthesis 11, any portion of the cement mantle 17 such as that overlying the enlarged shoulder 15 as indicated by the numeral 26 in FIG. 1, must be removed. As can be seen in FIG. 2, the restrictor 18 and centralizer 19 remain within the intramedullary canal 13 following removal of the prosthesis 11 as does the cement mantle 17 which retained the prosthesis 11.

It is desirable that all of the old cement 17 be removed prior to implantation of a new prosthesis in the intramedullary canal 13. In order to effect such cement removal efficiently and with minimal risk to the patient, the present invention provides guide means for the drill and reamer utilized for such removal. Referring to FIG. 3, there is shown a cannulated trail femoral component 30 of the present invention following its insertion into the cavity 25 left by removal of the original prosthesis 11. The cannulated trial femoral component 30 preferably has a stem 31 which is shaped substantially the same as the shape of the stem of the original prosthesis 11. The stem 31 extends from a distal end 32 to an enlarged upper end 34 extending out of the cavity 25. The stem 31 has a longitudinally extending passageway 33 which extends from the distal end 32 to the upper end 34 where it forms an outlet opening 35.

Prior to removal of the original prosthesis 11, X-rays should be taken to determine that the stem 12 of such original prosthesis was properly aligned to the intramedullary canal 13 and that is did not shift into varus as a result of subsidence within the cement mantle. Such subsidence within the cement mantle is known to occur over a period of time.

As shown in FIG. 4, there is provided a drill 40 having an elongated drill bit 41. The drill bit 41 has a length permitting it to extend completely through the longitudinal passageway 33 of the cannulated trail femoral component 30 and a substantial distance beyond. Thus, as shown in FIG. 4, the drill bit 41 is of sufficient length to drill, using the longitudinal passageway 33 as a guide, through the centralizer 19, restricter 18 and a substantial distance into the intramedullary canal 13 forming a new channel 42 below the restricter 18.

Referring not to FIG. 5, there is shown a built guide wire 43 having an enlarged head 44 positioned in the newly drilled channel 42.

Thus, following drilling of the channel 42 through the centralizer 19, restricter 18 and further into the intramedullary canal 13, the drill bit 41 is removed therefrom while leaving the cannulated trial femoral component 30 positioned therein. Thereafter, the guide wire 43 with its enlarged head 44 is inserted through the longitudinal passageway 33 and into the channel 42. Following insertion of the guide wire 43, the cannulated trial femoral component 30 is removed leaving the guide wire 43 in position.

Referring now to FIG. 6, following removal of the cannulated trial femoral component 30, a reamer 50 having a hollow stem 51 terminating in an enlarged cutting head 52 is provided. A longitudinal passageway 53 extends through the cutting head 52 and the stem 51. The reamer 50 is telescoped over the bullit guide wire 43 and may be power rotated by any standard well known power means.

As can be seen in FIGS. 7 and 8, progressively larger reamers 50' (FIG. 7) and 50" (FIG. 8) with progressively larger cutting heads 52' and 52" are utilized to progressively enlarge the opening of the cavity 25 and remove the old cement 17, the centralizer 19 and the restricter 18 and to progressively enlarge the opening until all of the old cement 17 has been removed and in doing so to utilized the bullit guide wire 43 to guide it. If desired, as progressively larger reamers 50, 50' and 50" are used, larger diameter guide wires may be inserted, replacing the small guide wire 43 used for the drill bit 41. The larger guide wires will give additional rigidity in guiding the path of the reamers.

Referring to FIG. 9, following reaming of the old cement 17 in the lower portion of the femur and reaming of the centralizer 19 and restricter 18, the reamer and guide wires 43 may be removed. Although there will be additional old cement 17 still present in the upper, larger femur portion, it can be readily removed by conventional techniques.

It is to be understood that the above detailed description of a preferred embodiment of the invention is provided by way of example only. Various details of design and construction and steps in the procedure may be modified without departing from the true spirit and scope of the invention as set forth in the appended claims.

We claim:

1. For use in performing revision surgery to replace a hip prosthesis having a stem portion previously implanted in a cement mantle in the medullary canal of a femur, the combination comprising:
   (a) a trail prosthesis having a stem extending from a distal end to a proximal end, said stem having a passageway extending longitudinally throughout its length from said distal end to said proximal end;
   (b) drill means sized to be received within said passageway for forming a pilot passageway in said medullary canal using the passageway of said trial prosthesis as a guide; and
   (c) cannulated reamer means sized to fit over said drill means for enlarging said pilot passageway following removal of said trial prosthesis using said drill means as a guide.

2. For use in performing revision surgery to replace a hip prosthesis having a stem portion previously implanted mantle in the medullary canal of a femur, the combination comprising:
   (a) a trial prosthesis having a stem extending from a distal end to a proximal end, said stem having a passageway extending longitudinally throughout its length from said distal end to said enlarged shoulder;
   (b) drill means sized to be received within said passageway for forming a pilot passageway in said medullary canal using the passageway of said trial prosthesis as a guide;
   (c) guide wire means sized for positioning in said pilot passageway; and
   (d) cannulated reamer means sized to fit over said drill means for enlarging said pilot passageway using said guide wire means as a guide.

3. The combination according to claim 2 further including a plurality of progressively larger cannulated reamer means.

4. The combination according to claim 2, wherein said guide wire means has an enlarged head.

5. The combination according to claim 2 further including at least one additional guide wire having greater size and rigidity than said guide wire means.

* * * * *